United States Patent [19]

Takagi et al.

[11] Patent Number: 4,855,497
[45] Date of Patent: Aug. 8, 1989

[54] NOVEL DIAMINE DERIVATIVES

[75] Inventors: Mitiro Takagi, Saitama; Yasuyuki Katoh, Kanagawa; Tomatsu Yamazaki, Saitama, all of Japan

[73] Assignee: Chugai Seiyaku Kaubshiki Kaisha, Tokyo, Japan

[21] Appl. No.: 840,681

[22] Filed: Mar. 18, 1986

[30] Foreign Application Priority Data

Apr. 2, 1985 [JP] Japan ................................ 60-69694

[51] Int. Cl.$^4$ ............................................ C07C 103/22
[52] U.S. Cl. ................................................... 564/182
[58] Field of Search ......................... 564/182; 514/617

[56] References Cited

U.S. PATENT DOCUMENTS

| | | | |
|---|---|---|---|
| 2,644,003 | 6/1953 | Gysin et al. | 564/194 X |
| 2,948,736 | 8/1960 | Martin | 564/194 X |
| 3,401,203 | 9/1968 | Kraiman et al. | 564/404 X |
| 3,732,253 | 5/1973 | Cavalleri et al. | 564/182 X |
| 3,803,211 | 4/1974 | Dolejes et al. | 564/404 X |
| 3,988,473 | 4/1976 | Adams et al. | 564/194 X |
| 3,989,834 | 11/1976 | Malen et al. | 564/194 X |
| 4,070,485 | 1/1978 | Malen et al. | 564/194 X |
| 4,080,452 | 3/1978 | Malen et al. | 564/194 X |
| 4,125,730 | 11/1978 | Hidaka et al. | 564/194 X |
| 4,187,318 | 2/1980 | Dreikorn | 564/404 X |
| 4,252,804 | 2/1981 | Joullié | 564/194 X |
| 4,360,465 | 11/1982 | Buschmann et al. | 564/182 X |
| 4,381,305 | 4/1983 | Casagrande et al. | 564/182 X |
| 4,536,346 | 8/1985 | Shepherd et al. | 564/182 X |
| 4,562,201 | 12/1985 | Stout et al. | 564/182 X |

FOREIGN PATENT DOCUMENTS

| | | | |
|---|---|---|---|
| 50-3512 | 2/1975 | Japan | 564/194 |
| 1423761 | 6/1976 | United Kingdom | 564/194 |
| 1423762 | 8/1976 | United Kingdom | 564/194 |

Primary Examiner—Paul F. Shaver
Attorney, Agent, or Firm—Browdy and Neimark

[57] ABSTRACT

A compound of the following general formula or a salt thereof

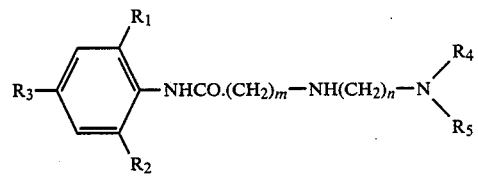

(wherein $R_1$ and $R_2$ which may be the same or different are each an alkyl group having 1 to 3 carbon atoms; $R_3$ is a hydrogen atom or an alkyl group having 1 to 3 carbon atoms; $R_4$ and $R_5$ which may be the same or different are each a hydrogen atom or an alkyl group having 1 to 8 carbon atoms; m and n which may be the same or different are ach an integer of 1 to 7; provided that $R_4$ and $R_5$ are not a hydrogen atom at the same time), and a process of preparing the same are disclosed.

The compound is sueful in the treatment of arrythmias because it exhibits desirably strong effects for treating arrythmias and minimum undesirable side effects.

13 Claims, No Drawings

NOVEL DIAMINE DERIVATIVES

DETAILED DESCRIPTION OF THE INVENTION

1. Field of the Invention

The present invention relates to novel diamine derivatives useful in the treatment of arrythmias.

2. Prior Art

The compounds claimed by the present invention are novel and have not been reported in literature.

PROBLEMS TO BE SOLVED BY THE INVENTION

Antiarrythmics currently used in clinical applications include lidocaine, disopyramide and procainamide. Lidocaine is suitable for intravenous or intramuscular administration (British Medical Journal, 2, 29-30, 1970, and The Merck Index, 10th Edition, 5304, 1983) and is not administered perorally for clinical purposes because the drug level in blood is too low to attain the desired effectiveness. Disopyramide is highly adapted for clinical use since it exhibits a sustained activity in peroral administration but it can cause various undesirable side effects [Chiryogaku (Therapeutics), vol. 11, No. 4, p. 512, 1983; and The Merck Index, 10th Edition, 3378, 1983]. Among the side effects that are caused by disopyramide are hydrodipsia, anuresis, constipation, vertigo, blurring of vision and vomiting, all of these presumably resulting from the anti-cholinergic action of disopyramide. High incidence of anuresis has been found in patients with prostatomegaly and neurotic bladders due to diabetes. Disopyramide also has an inhibitory action on the cardiac muscles and must be administered with great care to patients who are or may potentially be suffering from cardiac failure.

Procainamide is known to have the disadvanage of exhibiting anti-cholinergic and amyocardiac activities and causing hypotension (Medicina, vol. 20, No. 7, p. 1115, 1983; and Gekkan Yakuji, vol. 26, No. 5, p. 115, 1984).

The present inventors made concerted efforts to develop drugs that have minimum side effects while exhibiting potent antiarrythmic activity. As a result, they found that the compounds claimed by the present invention are free from all the defects of the existing antiarrythmics described above.

MEANS FOR SOLVING THE PROBLEMS

The compound of formula (I) of the present invention may be prepared by reacting a chloroalkylanilide derivative of formula (II) with a diamine derivative of formula (III) in an inert solvent in the presence of a base. The reaction scheme may be represented as follows:

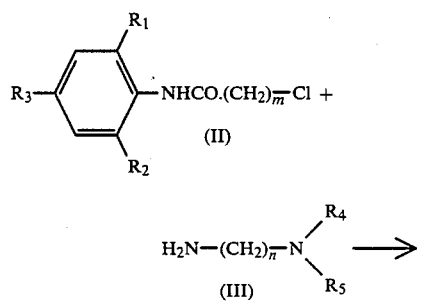

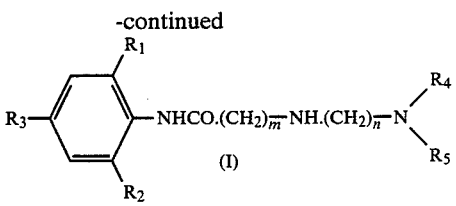

(where $R_1$ and $R_2$ which may be the same or different are each an alkyl group having 1 to 3 carbon atoms; $R_3$ is a hydrogen atom or alkyl group having 1 to 3 carbon atoms; $R_4$ and $R_5$ which may be the same or different are each a hydrogen atom, an alkyl group having 1 to 8 carbon atoms or a cycloalkyl group having 3 to 8 carbon atoms; m and n which may be the same or different are each an integer of 1 to 7; provided that $R_4$ and $R_5$ are not a hydrogen atom at the same time).

Although a solvent useful for the reaction of a chloroalkylanilide (II) with a diamine (II) includes solvents such as dichloromethane, chloroform, ethyl acetate, etc. which are usually used in a reaction similar to the above reaction, benzene, toluene and xylene are preferable.

The reaction may be carried out at a temperature from room temperature to a reflux temperature of the solvent used for about 3 to 24 hours while stirring the reaction system.

Although a base useful for the reaction includes organic bases such as trimethylamine, triethylamine, pyridine and the like, and inorganic bases such as potassium carbonate, sodium carbonate and the like, the organic bases are preferable.

Stated more specifically, $R_1$ and $R_2$ in formula (I) may be a methyl or ethyl group, with methyl being preferable; $R_3$ may be a hydrogen atom or a methyl group, with hydrogen being preferable; $R_4$ and $R_5$ may be a hydrogen atom, a methyl group, an ethyl group, an iso-propyl group, a n-butyl group, an iso-butyl group, a tert-butyl group, a n-hexyl group or a cyclooctyl group, with methyl, ethyl, iso-propyl and iso-butyl being preferable; m may be an integer of 2 to 5, with 2 or 3 being preferable; n may be an integer of 2 to 7, with 2 or 3 being preferable.

The compounds of the present invention may optionally be converted to the corresponding salts by routine methods.

The following referential example and working examples are provided for the purpose of illustrating the present invention but are by no means construed as limiting.

REFERENTIAL EXAMPLE

Synthesis of 3-chloro-2', 6'-dimethylpropionanilide

A mixture of 2,6-dimethylaniline (60.5 g) and potassium carbonate (45 g) is dissolved in a 3:1 mixture of ethyl acetate and water (1,200 ml). To the ice-cooled mixture, 100 ml of an ethyl acetate solution of 3-chloropropionyl chloride (52.5 ml) is added dropwise under agitation. The reaction mixture is stirred for 3 hours at room temperature and the aqueous layer is subsequently separated. The organic layer is washed with a saturated aqueous solution of sodium bicarbonate and a saturated aqueous solution of sodium chloride, and subsequently dried over Glauber's salt. Upon distilling off the solvent under vacuum, a colorless powder results. Recrystallization from ethanol provides a colorless needle in an amount of 96.5 g (yield: 90.8%). m.p. 131° C.

NMR (CDCl$_3$)δ: 2.10 (3Hx2s,PhCH$_3$), 2.68 (2H,t,J=7. OHz,C—2H), 3.74 (2H,t,J=7. OHz,C—3H), 6.92 (3H,s,PhH), 7.40 (1H,broad s,NH).

EXAMPLE 1

Synthesis of 3-(diisopropylaminoethylamino)-2',6'-dimethylpropionanilide (Compound No. 1)

A hundred milliliters of a toluene solution of a mixture of N,N-diisopropylethylenediamine (6.1 g), 3-chlor-2',6'-dimethylpropionanilide (3.6 g) and triethylamine (2.0 ml) is heated for 6 hours under reflux. After cooling, the reaction solvent is distilled off under vacuum. To the residue, 200 ml of chloroform is added and the mixture is washed with a saturated aqueous solution of sodium bicarbonate and a saturated aqueous solution of sodium chloride. After drying over Glauber's salt, the solvent is distilled off under vacuum, yielding a pale yellow powder. Recrystallization from n-hexane provides a colorless needle in an amount of 3.0 g (yield: 66.9%). m.p. 78.8° C.

Elemental analysis: Cal'd for C$_{19}$H$_{33}$N$_3$O (%): C 71.43, H 10.41, N 13.15; Found (%): C 71.25, H 10.44, N 13.17.

NMR (CDCl$_3$)δ: 0.94 (3Hx4,d,J=6. OHz, CHCH$_3$), 2.18 (3Hx2,s,PhCH$_3$), 2.40–2.70 (2Hx3,m,NCH$_2$), 2.75–3.20

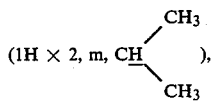

(1H × 2, m, CH(CH$_3$)(CH$_3$)), 2.96 (2H,t,J=6. OHz, COCH$_2$), 6.96 (3H,s,PhH), 10.00 (1H,broad s,NH).

An ethanol solution of the obtained free base is treated with HCl-saturated ether, yielding a colorless needle (dihydrochloride, hygroscopic). m.p. 198.3° C.

An ethanol solution of the same free base is treated with phosphoric acid, yielding a colorless needle (diphosphoric acid). m.p. 212.0° C.

Elemental analysis: Cal'd for C$_{19}$H$_{33}$N$_3$O·2H$_3$PO$_4$ (%): C 44.27, H 7.63, N 8.15; Found (%): C 44.47, H 7.68, N 8.24.

EXAMPLE 2

Synthesis of 3-(dimethylaminopropylamino)-2',6'-dimethylpropionanilide (Compound No. 2)

Sixty milliliters of a toluene solution of a mixture of N,N-dimethyl-1,3-propanediamine (3.74 ml), 3-chloro-2',6'-dimethylpropionanilide (2.12 g) and triethylamine (2.0 ml) is treated as in Example 1 to provide a colorless oil in an amount of 2.29 g (yield: 82.7%).

NMR (CDCl$_3$)δ: 2.12, 2.16 (each 3Hx2,s,PhCH$_3$, NCH$_3$), 2.96 (2H,t,J=5Hz,COCH$_2$), 6.95 (3H,s,PhH), 9.66 (1H,broad s,NH).

A hydrochloride of this compound is a colorless needle (hygroscopic) with a melting point of 201.3° C. A phosphate salt of the same compound is a colorless needle with a melting point of 219.8° C.

Elemental analysis: Cal'd for C$_{16}$H$_{27}$N$_3$O·2H$_3$PO$_4$ (%): C 40.60, H 7.03, N 8.88; Found (%): C 40.48, H 7.03, N 8.93.

EXAMPLE 3

Synthesis of 3-(diethylaminopropylamino)-2',6'-dimethylpropionanilide (Compound No. 3)

Sixty milliliters of a toluene solution of a mixture of N,N-disthyl-1,3-propanediamine (4.73 ml), 3-chloro-2',6'-dimethylpropionanilide (2.12 g) and triethylamine (2.0 ml) is treated as in Example 1 to provide a colorless oil in an amount of 2.2 g (yield: 72.1%).

NMR (CDCl$_3$)δ: 2.18 (3Hx2,s,PhCH$_3$), 2.30–3.10 (2Hx5,m,NCH$_2$), 2.96 (2H,t,J=5Hz,COCH$_2$), 6.97 (3H,s,PhH), 9.80 (1H,broad s,NH).

A hydrochloride of this compound is a colorless powder (hygroscopic) with a melting point of 81.3° C. A phosphate salt of the same compound is a colorless needle with a melting point of 187.2° C.

Elemental analysis: Cal'd for C$_{18}$H$_{31}$N$_3$O·2H$_3$PO$_4$·4/3H$_2$O (%): C 41.11, H 7.61, N 7.97; Found (%): C 40.95, H 7.48, N 8.47.

EXAMPLE 4

Synthesis of 3-(isopropylaminoethylamino)-2',6'-dimethylpropionanilide (Compound No. 4)

Three hundred milliliters of a toluene solution of a mixture of N-isopropyl-1,2-ethylenediamine (20.0 g), 3-chloro-2',6'-dimethylpropionanilide (13.9 g) and triethylamine (10 ml) is treated as in Example 1 to provide a pale yellow powder. Recrystallization from n-hexane provides a colorless needle in an amount of 11.5 g (yield: 63.2%). m.p. 69.5° C.

NMR (CDCl$_3$): 2.18 (9Hx2s,PhCH$_3$), 2.40–3.08

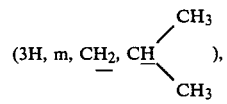

(3H, m, CH$_2$, CH(CH$_3$)(CH$_3$)), 6.96 (3H,s,PhH), 9.62 (1H,broad s,NH).

Elemental analysis: Cal'd for C$_{16}$H$_{27}$N$_3$O (%): C 69.28, H 9.81, N 15.15; Found (%): C 69.46, H 9.81, N 15.07.

A phosphate salt of this compound is a colorless needle with a melting point of 135.8° C.

Elemental analysis: Cal'd for C$_{16}$H$_{27}$N$_3$O·2H$_3$PO$_4$·H$_2$O (%): C 39.11, H 7.18, N 8.55; Found (%): C 39.61, H 6.90 N 8.71.

Compound Nos. 5 to 51 shown in Table 1 are produced by repeating the procedures of Example 1.

TABLE 1

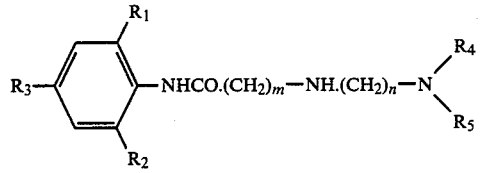

| Compound No. | $R_1$ | $R_2$ | $R_3$ | m | n | $R_4$ | $R_5$ | Nature | Salts acid | m.p. (°C.) |
|---|---|---|---|---|---|---|---|---|---|---|
| 5 | $CH_3$ | $CH_3$ | H | 2 | 2 | $CH_3$ | $CH_3$ | oil | $2.H_3PO_4$ | 230 |
| 6 | $CH_3$ | $CH_3$ | H | 2 | 2 | $C_2H_5$ | $C_2H_5$ | oil | $2.H_3PO_4$ | 213 |
| 7 | $CH_3$ | $CH_3$ | H | 2 | 2 | $i\text{-}C_4H_9$ | $i\text{-}C_4H_9$ | oil | $2.H_3PO_4$ | 162.8 |
| 8 | $CH_3$ | $CH_3$ | H | 2 | 2 | H | $t\text{-}C_4H_9$ | oil | $2.H_3PO_4$ | 161 |
| 9 | $CH_3$ | $CH_3$ | H | 2 | 2 | $n\text{-}C_4H_9$ | $n\text{-}C_4H_9$ | oil | $2.H_3PO_4$ | 163 |
| 10 | $CH_3$ | $CH_3$ | H | 2 | 2 | $n\text{-}C_6H_{13}$ | $n\text{-}C_6H_{13}$ | oil | $2.H_3PO_4$ | 164.1 |
| 11 | $CH_3$ | $CH_3$ | H | 2 | 3 | $i\text{-}C_3H_7$ | $i\text{-}C_3H_7$ | oil | $2.H_3PO_4$ | 192.3 |
| 12 | $CH_3$ | $CH_3$ | H | 2 | 3 | $i\text{-}C_4H_9$ | $i\text{-}C_4H_9$ | oil | $2.H_3PO_4$ | 179 |
| 13 | $CH_3$ | $CH_3$ | H | 2 | 3 | $n\text{-}C_4H_9$ | $i\text{-}C_4H_9$ | oil | $2.H_3PO_4$ | 114 |
| 14 | $CH_3$ | $CH_3$ | H | 2 | 3 | H | Cyclo-octyl | oil | $2.HCl$ | 179 |
| 15 | $CH_3$ | $CH_3$ | H | 2 | 4 | $i\text{-}C_3H_7$ | $i\text{-}C_3H_7$ | oil | $2.H_3PO_4$ | 165.8 |
| 16 | $CH_3$ | $CH_3$ | H | 2 | 4 | $i\text{-}C_4H_9$ | $i\text{-}C_4H_9$ | oil | $2.H_3PO_4$ | 126.5 |
| 17 | $CH_3$ | $CH_3$ | H | 2 | 5 | $i\text{-}C_4H_9$ | $i\text{-}C_4H_9$ | oil | $2.H_3PO_4$ | 147.2 |
| 18 | $CH_3$ | $CH_3$ | H | 3 | 3 | $i\text{-}C_4H_9$ | $i\text{-}C_4H_9$ | oil | $2.H_3PO_4$ | 116 |
| 19 | $CH_3$ | $CH_3$ | H | 3 | 3 | $C_2H_5$ | $C_2H_5$ | oil | $2.H_3PO_4$ | 208 |
| 20 | $CH_3$ | $CH_3$ | H | 5 | 2 | $i\text{-}C_3H_7$ | $i\text{-}C_3H_7$ | oil | $2.H_3PO_4$ | 192.6 |
| 21 | $CH_3$ | $CH_3$ | H | 5 | 3 | $CH_3$ | $CH_3$ | oil | $2.H_3PO_4$ | 121.8 |
| 22 | $CH_3$ | $CH_3$ | H | 5 | 3 | $C_2H_5$ | $C_2H_5$ | oil | $2.H_3PO_4$ | 104.1 |
| 23 | $C_2H_5$ | $C_2H_5$ | H | 2 | 2 | $CH_3$ | $CH_3$ | oil | $2.H_3PO_4$ | 176 |
| 24 | $C_2H_5$ | $C_2H_5$ | H | 2 | 2 | $C_2H_5$ | $C_2H_5$ | oil | $2.H_3PO_4$ | 183 |
| 25 | $C_2H_5$ | $C_2H_5$ | H | 2 | 2 | H | $i\text{-}C_3H_7$ | oil | $2.H_3PO_4$ | 194 |
| 26 | $C_2H_5$ | $C_2H_5$ | H | 2 | 2 | $i\text{-}C_3H_7$ | $i\text{-}C_3H_7$ | oil | $2.H_3PO_4$ | 204 |
| 27 | $C_2H_5$ | $C_2H_5$ | H | 2 | 2 | $i\text{-}C_4H_9$ | $i\text{-}C_4H_9$ | oil | $2.H_3PO_4$ | 154 |
|  |  |  |  |  |  |  |  |  | $2.HCl$ | 59 |
| 28 | $C_2H_5$ | $C_2H_5$ | H | 2 | 3 | $CH_3$ | $CH_3$ | oil | $2.H_3PO_4$ | 201 |
| 29 | $C_2H_5$ | $C_2H_5$ | H | 2 | 3 | $C_2H_5$ | $C_2H_5$ | oil | $2.H_3PO_4$ | 173 |
| 30 | $C_2H_5$ | $C_2H_5$ | H | 2 | 3 | $i\text{-}C_3H_7$ | $i\text{-}C_3H_7$ | oil | $2.H_3PO_4$ | 194 |
| 31 | $C_2H_5$ | $C_2H_5$ | H | 2 | 3 | $i\text{-}C_4H_9$ | $i\text{-}C_4H_9$ | oil | $2.H_3PO_4$ | 179 |
| 32 | $C_2H_5$ | $C_2H_5$ | H | 2 | 3 | $n\text{-}C_4H_9$ | $n\text{-}C_4H_9$ | oil | $2.H_3PO_4$ | 180 |
| 33 | $C_2H_5$ | $C_2H_5$ | H | 2 | 4 | $i\text{-}C_3H_7$ | $i\text{-}C_3H_7$ | oil | $2.HCl$ | 47 |
| 34 | $C_2H_5$ | $C_2H_5$ | H | 2 | 4 | $i\text{-}C_4H_9$ | $i\text{-}C_4H_9$ | oil | $2.H_3PO_4$ | 147 |
| 35 | $C_2H_5$ | $C_2H_5$ | H | 2 | 5 | $i\text{-}C_4H_9$ | $i\text{-}C_4H_9$ | oil | $2.H_3PO_4$ | 171.4 |
| 36 | $C_2H_5$ | $C_2H_5$ | H | 2 | 7 | $i\text{-}C_4H_9$ | $i\text{-}C_4H_9$ | oil | $2.H_3PO_4$ | 76 |
| 37 | $C_2H_5$ | $C_2H_5$ | H | 3 | 2 | $i\text{-}C_3H_7$ | $i\text{-}C_3H_7$ | oil | $2.H_3PO_4$ | 114 |
| 38 | $CH_3$ | $CH_3$ | $CH_3$ | 2 | 2 | $CH_3$ | $CH_3$ | oil | $2.H_3PO_4$ | 184 |
| 39 | $CH_3$ | $CH_3$ | $CH_3$ | 2 | 2 | $C_2H_5$ | $C_2H_5$ | oil | $2.H_3PO_4$ | 149 |
| 40 | $CH_3$ | $CH_3$ | $CH_3$ | 2 | 2 | H | $i\text{-}C_3H_7$ | oil | $2.H_3PO_4$ | 180 |
| 41 | $CH_3$ | $CH_3$ | $CH_3$ | 2 | 2 | $i\text{-}C_3H_7$ | $i\text{-}C_3H_7$ | oil | $2.H_3PO_4$ | 216 |
| 42 | $CH_3$ | $CH_3$ | $CH_3$ | 2 | 2 | $i\text{-}C_4H_9$ | $i\text{-}C_4H_9$ | oil | $2.H_3PO_4$ | 161 |
| 43 | $CH_3$ | $CH_3$ | $CH_3$ | 2 | 2 | $n\text{-}C_4H_9$ | $n\text{-}C_4H_9$ | oil | $2.H_3PO_4$ | 157 |
| 44 | $CH_3$ | $CH_3$ | $CH_3$ | 2 | 3 | $CH_3$ | $CH_3$ | oil | $2.H_3PO_4$ | 208 |
| 45 | $CH_3$ | $CH_3$ | $CH_3$ | 2 | 3 | $C_2H_5$ | $C_2H_5$ | oil | $2.H_3PO_4$ | 214 |
| 46 | $CH_3$ | $CH_3$ | $CH_3$ | 2 | 3 | $i\text{-}C_3H_7$ | $i\text{-}C_3H_7$ | oil | $2.H_3PO_4$ | 188 |
| 47 | $CH_3$ | $CH_3$ | $CH_3$ | 2 | 3 | $i\text{-}C_4H_9$ | $i\text{-}C_3H_9$ | oil | $2.H_3PO_4$ | 175 |
| 48 | $CH_3$ | $CH_3$ | $CH_3$ | 2 | 3 | $n\text{-}C_4H_9$ | $n\text{-}C_4H_9$ | oil | $2.H_3PO_4$ | 137 |
| 49 | $CH_3$ | $CH_3$ | $CH_3$ | 2 | 4 | $i\text{-}C_4H_9$ | $i\text{-}C_4H_9$ | oil | $2.H_3PO_4$ | 140 |
| 50 | $CH_3$ | $CH_3$ | $CH_3$ | 3 | 2 | $i\text{-}C_3H_7$ | $i\text{-}C_3H_7$ | oil | $2.H_3PO_4$ | 203 |
| 51 | $CH_3$ | $CH_3$ | $CH_3$ | 3 | 3 | $n\text{-}C_4H_9$ | $n\text{-}C_4H_9$ | oil | $2.H_3PO_4$ | 188 |

The compounds of the present invention exhibit a marked antiarrythmic activity with reduced side effects.

The following are the results of experiments conducted to demonstrate the advantages of these compounds which were used in the form of corresponding salts unless otherwise noted.

EXPERIMENT 1

Activity Aganist Chloroform-Induced Arrythmia in Rats

The following procedures were substantially in accordance with the method of Erker and Baker (Arch. Int. Pharmacodyn., 243, 97–102, 1980). Aminophylline (20 mg/kg) was injected intramuscularly into two groups of Sprague-Dowley male rats (3–4 wk. old, 7 animals per group) weighing about 100 g on average, one group having been starved for 24 hours and the other group not starved. Thirty minutes after the injection, the animals were put into a 4,000-ml glass beaker with a lid that contained gauze impregnated with 200 ml of chloroform. Fifty minutes later, the animals were recovered from the beaker and their chests were incised to check their hearts for the presence of ventricular fibrillation. The features of their cardiac rhythm were examined by the electrocardiogram. When no distinct fibrillation was observed, the heart was touched with tweezers. The heart was identified as fibrillar when rapid irregular twitchings occured on the surface of ventricles and continued for at least 5 seconds after chest incision or mechanical stimulation.

Selected compounds suspended in 3% gum arabic were administered in various doses to the rats either intraperitoneally (i.P.) or perorally (P.O.) 30 minutes prior to treatment with chloroform. The percent prevention of ventricular fibrillation was determined for each rat. Only a 3% gum arabic solution was administered to the control group. The results are shown in Table 2.

TABLE 2

| Compound No. | Dose (mg/kg) | Route of administration | Percent prevention Starved | Percent prevention Not starved |
| --- | --- | --- | --- | --- |
| Control | — | — | 21.8 | 19.6 |
| Lidocaine | 20 | i.P. | 77.1 | — |
| Disopyramide | 10 | P.O. | 49.6 | 37.6 |
| 1 | 25 | i.P. | — | 85.7 |
| 1 | 1 | P.O. | 85.7 | 85.7 |
| 2 | 1 | P.O. | — | 71.4 |
| 3 | 1 | P.O. | — | 100.0 |
| 4 | 1 | P.O. | — | 100.0 |
| 11 | 1 | P.O. | — | 85.7 |
| 12 | 1 | P.O. | — | 85.7 |
| 14 | 1 | P.O. | — | 85.7 |
| 31 | 1 | P.O. | — | 100.0 |
| 35 | 1 | P.O. | — | 100.0 |

EXPERIMENT 2

Activity Against Aconitine-Induced Arrythmia in Rats

Using Sprague-Dowley male rats (9-10 wk. old, two animals per group) weighing about 350 g on average, the following experiment was conducted substantially in compliance with the method of Vargftig et al. (Europ. J. Pharmacol., 6, 49, 1969).

The animals were anesthetized by intraperitoneal administration of 1 g/kg of urethane. A polyethylene cannula was inserted into both the femoral artery and vein of each animal; the drug was administered through the femoral vein while the blood pressure was measured at the femoral artery.

While the aconitine solution was continuously infused into the vein at a rate of 1 μg/kg/min, a selected compound was administered intravenously at 5-minute intervals. In order to prevent the aconitine-induced dyspnea from interfering with the experimental results, 0.2 mg/kg of d-tubocurarine was administered intravenously to each animal, which then was subjected to artificial respiration through a cannula inserted into the trachea (80 breathings/min, with 4 ml of air supplied by a single ventilation).

Identification of arrythmia was made by the ECG in the second induction period; the appearance of a QRS complex with sharply downward deflections was used as an indication of ventricular arrythmia and observation was continued until ventricular fibrillation appeared. The results are shown in Table 3 in terms of the times required for ventricular extrasystole and ventricular fibrillation to occur.

TABLE 3

| Compound No. | Dose (mg/kg) | Ventricular extrasystole (min) | Ventricular fibrillation (min) |
| --- | --- | --- | --- |
| Untreated | — | 14.3 | 35.3 |
| Disopyramide | 10 | 22.6 | 78.2 |
| 1 | 5 | 45.2 | >120.0 |
| 2 | 5 | 25.5 | 36.5 |
| 3 | 5 | 27.4 | >120.0 |
| 4 | 10 | 34.4 | >120.0 |
| 11 | 5 | 26.2 | 73.8 |
| 11 | 10 | 44.2 | >120.0 |
| 12 | 5 | 26.2 | 30.2 |
| 31 | 5 | 26.1 | >90.0 |

TABLE 3-continued

| Compound No. | Dose (mg/kg) | Ventricular extrasystole (min) | Ventricular fibrillation (min) |
| --- | --- | --- | --- |
| 35 | 5 | 24.5 | 84.5 |

EXPERIMENT 3

Activity Against Ouabain-Induced Arrythmia in Guinea Pigs

Hartly male guinea pigs (5-6 wk. old, two animals per group) weighing about 350 g on average were anesthetized by intraperitoneal administration of 1.2 g/kg of urethane. A polyethylene cannula was inserted into both the cervical vein and the carotid artery; the drug was administered through the cervical vein while the blood pressure was measured at the carotid artery. A selected test compound was administered 5 minutes before the sustained intravenous infusion of the ouabain solution (5 μg/kg/min) as described in J. Pharmacol. Exp. Ther., 136, 227, 1962). Identification of arrythmia was made by the ECG in the second induction period; the appearance of a QRS complex with sharply downward deflictions was used as an indication of ventricular arrythmia and observation was continued until ventricular fibrillation and cardiac arrest appeared. The results are shown in Table 4 in terms of the times required for ventricular extrasystole, ventricular fibrillation and cardiac arrest to occur.

TABLE 4

| Compound No. | Dose (mg/kg) | Ventricular extrasystole (min) | Ventricular fibrillation (min) | Cardiac arrest (min) |
| --- | --- | --- | --- | --- |
| Untreated | — | 28.5 | 35.1 | 41.2 |
| Disopyramide | 10 | 41.1 | 54.3 | 59.6 |
| 1 | 5 | 42.1 | 45.4 | 51.3 |
| 2 | 5 | 31.0 | 38.5 | 39.5 |
| 2 | 10 | 38.1 | 43.4 | 48.7 |
| 3 | 10 | 34.4 | 42.2 | 48.4 |
| 4 | 10 | 42.5 | 59.5 | 66.5 |
| 11 | 10 | 35.3 | 45.3 | 52.4 |
| 12 | 10 | 45.4 | 48.2 | 56.6 |
| 31 | 5 | 34.1 | 51.0 | 57.8 |
| 35 | 5 | 45.4 | 48.4 | 56.2 |

EXPERIMENT 4

Activity Against Acetylcholine (I)

SD/Slc male rats (10-mo. old, four animals per group) were clubbed dead and their ilea were immediately extracted. The ilea were suspended under a load of 1 g in a Krebs-Henseleit solution oxygenated with a mixture of 95% $O_2$ + 5% $CO_2$ at 27° C., and the ileal reaction was measured isotonically.

The anti-cholinergic activity of each of the compounds tested was determined in terms of percent inhibition against the contractive reaction of $10^{-6}M$ of acetylcholine (causing 60-70% of the maximum contractive reaction of acetylcholine). The results are shown in Table 5.

TABLE 5

| Compound No. | Dose (M) | Percent inhibition |
| --- | --- | --- |
| Atropine | $10^{-8}$ | 100 |
| Disopyramide | $10^{-4}$ | 89 |
| 1 | $10^{-4}$ | 20 |
| 2 | $10^{-4}$ | 7 |
| 3 | $10^{-4}$ | 28 |

TABLE 5-continued

| Compound No. | Dose (M) | Percent inhibition |
| --- | --- | --- |
| 4 | $10^{-4}$ | 0 |
| 11 | $10^{-4}$ | 0 |
| 18 | $10^{-4}$ | 0 |
| 35 | $10^{-4}$ | 9 |

EXPERIMENT 5

Activity Against Acetylcholine (II)

Beagle dogs were anesthetized by intravenous administration of pentobarbital (35 mg/kg). The following experiment was conducted in accordance with the method of Sato et al. (Tohoku J. Exp. Med., 108, 377–388, 1982). The left lower jaw of each animal was incised to identify the submandibular gland, the duct through which saliva was excreted from that gland, and the artery nourishing the same gland. A polyethylene tube was first inserted into the excretory duct. Then, a cannula was inserted into the submandibular gland controlling artery and said gland was perfused with the arterial blood drawn from the femoral artery. The tube from the duct was connected to a drop counter and the number of drops of excreted saliva was recorded. The excretion of saliva was induced by intra-arterial administration of acetylcholine.

One minute before the acetylcholine administration, 100 g (0.1 ml) of a selected compound was administered intra-arterially and its ability to inhibit saliva excretion was examined. The results are shown in Table 6.

TABLE 6

| Compound No. | Dose (g) | Percent inhibition |
| --- | --- | --- |
| Atropine | 1 | 42.9 |
| Disopyramide | 100 | 41.7 |
| 1 | 100 | 0 |

EXPERIMENT 6

Effect on the Time of Sleeping Induced by Hexobarbital

A selected compound of the present invention was administered perorally to ddY/Slc male rats (5–6 wk. old, 10 animals per group) in an amount of 50 or 100 mg/kg. One hour later, 2.5 mg/kg of hexobarbital was administered intraperitoneally to each animal, thereby causing the loss of orthogonal reflex. The time required for the recovery of orthogonal reflex was measured for each animal.

As comparative drugs, 50 or 100 mg/kg of disopyramide and 5 mg/kg of diazepam were administered perorally. The results are shown in Table 7.

TABLE 7

| Compound No. | Salt | Dose (mg/kg) | Time of sleeping, min (mean ± S.E.) |
| --- | --- | --- | --- |
| Untreated | — | — | 53.9 ± 2.7 |
| Disopyramide | $H_3PO_4$ | 50 | 59.8 ± 3.3 |
| Disopyramide | $H_3PO_4$ | 100 | 53.5 ± 2.4 |
| Diazepam | — | 5 | 136.4 ± 5.8** |
| 1 | free | 50 | 47.8 ± 2.8 |
| 1 | free | 100 | 58.2 ± 5.1 |
| 1 | HCl | 100 | 50.0 ± 2.8 |
| 2 | $H_3PO_4$ | 50 | 54.1 ± 3.7 |
| 3 | $H_3PO_4$ | 50 | 54.0 ± 2.4 |
| 3 | $H_3PO_4$ | 100 | 52.4 ± 2.6 |
| 4 | $H_3PO_4$ | 50 | 50.9 ± 2.4 |
| 4 | $H_3PO_4$ | 100 | 55.0 ± 3.9 |

**$p < 0.05$ (level of significant difference from the time of sleeping of the untreated group)

EXPERIMENT 7

Effect on Blood Sugar Level

After starving SD/Slc male rats (body weight, 250 g; 6 animals per group) overnight, 20-µl blood samples were drawn from the tail vein of each rat while it was not anesthetized. Records were taken of the sugar level in each blood sample. A selected compound of the present invention was suspended in 3% gum arabic and the suspension was administered perorally to each rat in an amount of 50 or 200 mg/kg. At 2, 4 and 6 hours of the administration, blood samples were taken and their blood sugar levels were measured. Measurements of blood sugar levels were conducted with a New Blood Sugar Test (Boehringer, Mannheim).

To the control group, a 3% gum arabic solution was administered, and diisopyramide was administered as a comparative drug. The results are shown in Table 8.

TABLE 8

| Compound No. | Dose (mg/kg) | Blood sugar level | | | |
| --- | --- | --- | --- | --- | --- |
| | | 0 hr (mg/dl) | 2 hr (mg/dl) | 4 hr (mg/dl) | 6 hr (mg/dl) |
| Control | — | 63.6 ± 3.7 | 62.7 ± 5.6 | 54.1 ± 3.9 | 62.9 ± 3.1 |
| Disopyramide | 50 | 75.2 ± 5.9 | 46.9 ± 1.7* | 41.9 ± 2.9* | 45.8 ± 2.0*** |
| Disopyramide | 200 | 64.5 ± 5.6 | 41.7 ± 3.1** | 29.7 ± 3.2*** | 36.9 ± 2.6*** |
| 1 | 50 | 68.4 ± 4.0 | 63.0 ± 4.1 | 58.1 ± 2.2 | 59.9 ± 2.6 |
| 1 | 200 | 83.7 ± 3.0 | 55.4 ± 5.7 | 73.4 ± 7.2 | 71.2 ± 3.2 |
| 2 | 50 | 77.6 ± 5.5 | 61.3 ± 2.2 | 63.7 ± 4.5 | 64.4 ± 4.4 |
| 2 | 200 | 76.1 ± 2.4 | 52.9 ± 3.2 | 58.3 ± 2.6 | 56.8 ± 1.7 |
| 4 | 50 | 81.2 ± 2.4 | 60.3 ± 3.4 | 57.5 ± 1.6 | 61.5 ± 0.6 |
| 4 | 200 | 69.1 ± 2.9 | 57.4 ± 3.0 | 58.5 ± 2.1 | 59.0 ± 1.8 |
| 11 | 50 | 71.3 ± 2.9 | 61.8 ± 3.1 | 64.0 ± 2.2 | 63.8 ± 1.5 |
| 11 | 200 | 62.3 ± 2.7 | 52.0 ± 3.5 | 53.8 ± 3.8 | 63.6 ± 1.5 |

(mean ± S.E.)
*$p < 0.05$;
**$p < 0.01$;
*** $p < 0.001$
(levels of significant difference from the values in the control group at 0, 2, 4 and 6 hours)

As is demonstrated by the experimental results shown above, the compounds of the present invention have a broad spectrum of effectiveness for the treatment of arrythmias originating in both the ventricle and atrium. In particular, the compounds exhibited a sustained anti-arrythmic activity over a prolonged period. They have no such side effects as anti-cholinergic activity, central nerve depressant activity and the blood sugar reducing activity which is undesirable in the treatment of arrythmias. Therefore, the compounds of the present invention have potential for use as highly safe and effective antiarrythmic agents.

What is claimed is:

1. A compound of the following general formula or a salt thereof:

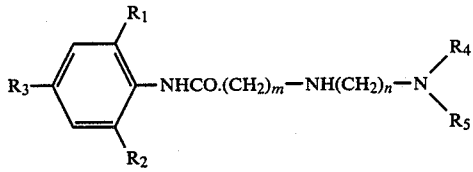

wherein $R_1$ and $R_2$ which may be the same or different are each an alkyl group having 1 to 3 carbon atoms; $R_3$ is a hydrogen atom or an alkyl group having 1 to 3 carbon atom; $R_4$ and $R_5$ which may be the same or different are each a hydrogen atom or an alkyl group having 1 to 8 carbon atoms or a cycloalkyl group having 3 to 8 carbon atoms; n is an integer of 1 to 7; and m is an integer of 2 to 5; provided that $R_4$ and $R_5$ are not both a hydrogen atom at the same time.

2. A compound according to claim 1 wherein $R_1$ and $R_2$ are methyl or ethyl group, $R_3$ is hydrogen or a methyl group; and n is an integer of 2 to 7.

3. A compound according to claim 1 wherein $R_1$ and $R_2$ are a methyl group; $R_3$ is a hydrogen atom; m and n which may be the same or different are each an integer of 2 or 3; and $R_4$ and $R_5$ which may be the same or different are each a methyl, ethyl, iso-propyl or iso-butyl group.

4. A process for preparing a compound of the formula:

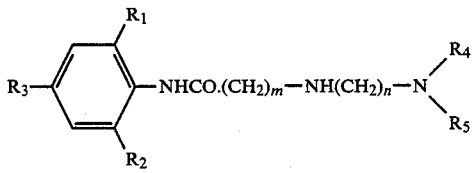

(where $R_1$ and $R_2$ which may be the same or different are each an alkyl group having 1 to 3 carbon atoms; $R_3$ is a hydrogen atom or an alkyl group having 1 to 3 carbon atoms; $R_4$ and $R_5$ which may be the same or different are each a hydrogen atom, an alkyl group having 1 to 8 carbon atoms or a cycloalkyl group having 3 to 8 carbon atoms; m and n which may be the same or different are each an integer of 1 to 7; provided that $R_4$ and $R_5$ are not a hydrogen atom at the same time) which comprises reacting a chloroalkylanilide derivative of the formula:

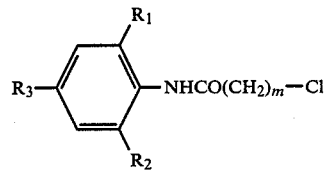

wherein $R_1$, $R_2$, $R_3$ and m are as defined above, with a diamine derivative of the formula:

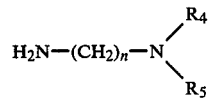

wherein $R_4$, $R_5$ and n are as defined above.

5. A process according to claim 4 wherein said reaction is carried out in an inert solvent in the presence of a base at an elevated temperature.

6. A process according to claim 5 wherein said inert solvent is selected from the group consisting of benzene, toluene, xylene, dichloromethane, chloroform and ethyl acetate, and said base is selected from the group consisting of trimethylamine, triethylamine, pyridine, potassium carbonate and sodium carbonate.

7. A process according to claim 6 wherein said reaction is carried out at a temperature of from 20° C. to 150° C.

8. A process according to claim 6 wherein said reaction is carried out in the presence of triethylamine in toluene at a reflux temperature.

9. A compound according to claim 1 wherein $R_1$ and $R_2$ are each a methyl group; $R_3$ is a hydrogen atom; m and n which may be the same or different are each an integer of 2 or 3; and $R_4$ and $R_5$ which may be the same or different are each a hydrogen atom, methyl, ethyl, iso-propyl or iso-butyl group; provided that $R_4$ and $R_5$ are not both a hydrogen atom at the same time.

10. A pharmaceutical composition in a form suitable for internal administration for treating arrythmias, comprising an arrrythmia-effective amount of a compound according to claim 1 together with a pharmaceutically acceptable carrier for internal administration.

11. A pharmaceutical composition in a form suitable for internal administration for treating arrythmias, comprising an arrythmia-effective amount of a compound according to claim 9 together with a pharmaceutically acceptable carrier.

12. A method of treating arrythmias in a patient in need of such therapy, comprising internally administering to said patient an arrythmia-effective amount of a compound according to claim 1.

13. A method of treating arrythmias in a patient in need of such therapy, comprising internally administering to said patient an arrythmia-effective amount of a compound according to claim 9.

* * * * *